(12) United States Patent
Matsuo et al.

(10) Patent No.: US 7,935,235 B2
(45) Date of Patent: May 3, 2011

(54) GAS SENSOR WITH SEALING STRUCTURE

(75) Inventors: Kouji Matsuo, Aichi (JP); Satoshi Ishikawa, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 678 days.

(21) Appl. No.: 11/971,705

(22) Filed: Jan. 9, 2008

(65) Prior Publication Data

US 2008/0116068 A1 May 22, 2008

Related U.S. Application Data

(62) Division of application No. 10/875,272, filed on Jun. 25, 2004, now Pat. No. 7,341,650.

(30) Foreign Application Priority Data

Jun. 27, 2003 (JP) .................................. 2003-185724

(51) Int. Cl.
*G01N 27/407* (2006.01)
(52) U.S. Cl. ........................................ 204/428; 73/23.31
(58) Field of Classification Search .................. 204/424, 204/428; 73/23.31, 23.32
See application file for complete search history.

(56) References Cited

U.S. PATENT DOCUMENTS

| | | | |
|---|---|---|---|
| 4,802,369 A * | 2/1989 | Morii | .......................... 73/114.73 |
| 4,986,892 A | 1/1991 | Kato et al. | |
| 5,039,972 A | 8/1991 | Kato et al. | |
| 5,795,454 A | 8/1998 | Friese et al. | |
| 5,948,963 A | 9/1999 | Kato et al. | |
| 6,206,377 B1 | 3/2001 | Weyl | |
| 6,273,432 B1 | 8/2001 | Weyl et al. | |
| 6,546,783 B2 | 4/2003 | Shirai | |
| 6,550,309 B1 | 4/2003 | Noda et al. | |
| 6,637,256 B2 | 10/2003 | Shirai | |
| 6,673,224 B2 | 1/2004 | Shirai | |
| 2002/0000116 A1* | 1/2002 | Kimata et al. | ............... 73/31.05 |
| 2003/0015020 A1 | 1/2003 | Geier et al. | |
| 2004/0040843 A1 | 3/2004 | Weyl et al. | |

FOREIGN PATENT DOCUMENTS

| | | |
|---|---|---|
| JP | 2-146362 U | 12/1990 |
| JP | 2-146363 U | 12/1990 |
| JP | 9-127047 A | 5/1997 |
| JP | 9-166572 A | 6/1997 |
| JP | 10-253578 A | 9/1998 |
| JP | 10-318980 A | 12/1998 |
| JP | 2001-324468 A | 11/2001 |
| JP | 2002-82089 A | 3/2002 |
| JP | 2002-202279 A | 7/2002 |

* cited by examiner

*Primary Examiner* — Kaj K Olsen
(74) *Attorney, Agent, or Firm* — Sughrue Mion, PLLC

(57) ABSTRACT

In a method of manufacturing a sensor, firstly, a plate-type detection element is inserted through an element-insertion through-hole of a first powder-compacted ring. Secondly, a flange section including at least the first powder-compacted ring is integrally assembled to the plate-type detection element, applying axially compressive pressure to the first powder-compacted ring so as to compressively deform the first powder-compacted ring such that the cross-sectional area of the element-insertion through-hole is reduced. Thirdly, the flange section is engaged, directly or via an intermediate member, with the stepped portion of the metallic shell at the time of disposing of the plate-type detection element in the through-hole of the metallic shell. A sensor prepared by the method is also disclosed.

1 Claim, 10 Drawing Sheets

GAS SENSOR WITH SEALING STRUCTURE

CROSS-REFERENCE TO RELATED PATENT APPLICATION

This is a divisional of U.S. application Ser. No. 10/875,272, now U.S. Pat. No. 7,341,650, filed Jun. 25, 2004, which claims priority from Japanese Patent Application No. 2003-185724, filed Jun. 27, 2003. The entire disclosures of the prior applications are incorporated herein by reference in their entirety.

BACKGROUND OF THE INVENTION

1. Field of the Invention

The present invention relates to a method of manufacturing a sensor and a sensor.

2. Description of the Related Art

Conventionally known sensors include oxygen sensors configured such that a detection element assuming a tubular shape (hereinafter also referred to as a tubular detection element) is housed in a metallic shell. Some oxygen sensors employ a tubular detection element having a flange portion, which is integrally formed at a substantially central position in the axial direction such that the flange portion faces rearward and projects radially outward. The tubular detection element is disposed in the metallic shell such that the flange portion is engaged directly or via another member (such as a packing) with a stepped portion projecting radially inward from the wall surface of a through-hole of the metallic shell.

Meanwhile, recently proposed oxygen sensors employ a detection element having a plate shape (a detection element having a laminated structure; hereinafter also referred to as a plate-type detection element) in place of a detection element having a tubular shape. Such a plate-type detection element does not have an integrally formed flange portion for engaging a stepped portion of a metallic shell. Thus, the plate-type detection element employs a tubular insulator on which an engagement surface is formed for engaging the stepped portion of the metallic shell, so that the plate-type detection element can be held by the metallic shell. More specifically, the insulator and the plate-type detection element are fixedly united, and the engagement surface of the insulator serves as the engagement surface of the flange portion and is engaged with the stepped portion of the metallic shell, whereby the plate-type detection element is held by the metallic shell (refer to Patent Document 1).

Use of the insulator as a flange portion enables attachment of a plate-type detection element to a metallic shell designed for use with a tubular detection element. Thus, sensors employing a tubular detection element and sensors using a plate-type detection element can share metallic shells as common components. Such sharing of components reduces component costs in the production of sensors.

Meanwhile, some oxygen sensors that employ a detection element having a plate shape are configured such that an insulating holder, a powder-compacted filler, and an insulating sleeve are arranged in layers so as to surround the plate-type detection element from all radial directions. In the process of manufacturing such a sensor, after the insulating holder and the powder-compacted filler are disposed within a metallic shell, a plate-type detection element to which the insulating sleeve is attached is inserted through an element-insertion through-hole of the powder-compacted filler and through an element-insertion through-hole of the insulating holder, whereby the plate-type detection element and the metallic shell are joined together. Subsequently, pressure is applied to the powder-compacted filler. Compression stress of the powder-compacted filler causes the plate-type detection element to be held in the metallic shell, thereby uniting the plate-type detection element and the metallic shell (refer to Patent Document 2).

[Patent Document 1]
Japanese Patent Application Laid-Open (kokai) No. 2002-174622 (FIGS. 1 and 3)
[Patent Document 2]
Japanese Patent Application Laid-Open (kokai) No. 2002-168823 (FIG. 1)

3. Problems to be Solved by the Invention

However, the conventional oxygen sensor disclosed in above-mentioned Patent Document 1 employs a glass seal material to fixedly join the insulator and the detection element. Glass welding requires high-temperature thermal processing. Since high-temperature thermal processing may crack (fracture) the detection element with an abrupt change in temperature, thermal processing time must be set long with a slow rate of raising the temperature so as to prevent fracturing of the detection element. However, in the process of manufacturing a sensor, increasing the high-temperature thermal processing time reduces manufacturing efficiency.

Meanwhile, the conventional oxygen sensor disclosed in above-mentioned Patent Document 2 employs a powder-compacted filler (a ring member formed through compaction of a powder substance (hereinafter also referred to as a powder-compacted ring)) in place of the glass seal material, thereby eliminating the need of a thermal processing step for glass welding and thus avoiding reduced sensor manufacturing efficiency, which could otherwise result from increasing the high-temperature thermal processing time.

The powder-compacted ring can be formed into, for example, an annular shape having an element-insertion through-hole formed at a central portion. The element-insertion through-hole has a cross-sectional area slightly greater than that of the plate-type detection element so as to allow insertion of the plate-type detection element therethrough.

However, in manufacturing a sensor that uses a powder-compacted ring having an element-insertion through-hole formed in the above-mentioned shape, the following assembly work becomes troublesome: after the powder-compacted ring is disposed in a through-hole of a metallic shell, a plate-type detection element and the metal shell are assembled together such that the detection element is inserted into the element-insertion through-hole of the powder-compacted ring. Specifically, when the plate-type detection element is to be inserted into the element-insertion through-hole, the plate-type detection element must be set to an angular orientation (an angular position around its axis) so as to be insertable into the element-insertion through-hole. Particularly, in the case of a metallic shell configured such that the powder-compacted ring is disposed deep in its through-hole, identifying the angular orientation of the element-insertion through-hole of the powder-compacted ring becomes difficult; as a result, assembling the plate-type detection element and the metallic shell becomes troublesome.

SUMMARY OF THE INVENTION

The present invention has been accomplished in view of the above problems, and an object of the present invention is to provide a method of manufacturing a sensor, which method comprises forming a flange section (an engagement section) on a detection element for engaging a stepped portion of the metallic shell, and facilitates attaching the detection element to the metallic shell.

The above object has been achieved in a first embodiment (1) of the invention, by providing a method of manufacturing a sensor comprising a plate-type detection element assuming the shape of an axially extending plate and having a detection portion formed at a front end portion directed toward an object to be measured, and an electrode terminal portion formed at a rear end portion thereof; a flange section integrally assembled to the plate-type detection element so as to surround the plate-type detection element; and a metallic shell having an axially extending through-hole for allowing the plate-type detection element to extend therethrough, and a stepped portion projecting radially inward from a wall surface of the through-hole and adapted for engaging the flange section. The flange section comprises at least a first powder layer formed from a first powder-compacted ring and is integrally assembled to the plate-type detection element. The method comprises a first step of inserting the plate-type detection element through an element-insertion through-hole of the first powder-compacted ring and positioning the first powder-compacted ring along an axial direction of the plate-type detection element, a cross-sectional area of the element-insertion through-hole being greater than that of the plate-type detection element as measured by sectioning in a plane perpendicular to the axial direction, and comparing at a stage before inserting the plate-type detection element through the first powder-compacted ring; a second step of integrally assembling the flange section including at least the first powder-compacted ring to the plate-type detection element, by applying axially compressive pressure to the first powder-compacted ring so as to compressively deform the first powder-compacted ring such that the cross-sectional area of the element-insertion through-hole is reduced; and a third step of engaging the flange section, directly or via an intermediate member, with the stepped portion of the metallic shell at the time of disposing the plate-type detection element in the through-hole of the metallic shell, to thereby axially position the plate-type detection element in the through-hole, the intermediate member having a hollow portion whose size is sufficiently large for the plate-type detection element to rotate about an axially extending center axis within the hollow portion.

According to the above method of manufacturing a sensor, in the first step, the plate-type detection element is inserted through the element-insertion through-hole of the first powder-compacted ring, and the first powder-compacted ring is positioned along the axial direction of the plate-type detection element.

In the second step, the flange section including at least the first powder-compacted ring is integrally assembled to the plate-type detection element, by means of applying pressure to the first powder-compacted ring so as to compressively deform the first powder-compacted ring such that the cross-sectional area of the element-insertion through-hole is reduced. As a result, the flange section including the first powder-compacted ring is integrally assembled to the plate-type detection element while projecting from the plate-type detection element in a direction perpendicular to the axial direction (radially outward), so that the flange section can engage the stepped portion of the metallic shell.

In the third step, at the time of disposing the plate-type detection element in the through-hole of the metallic shell, the flange section engages the stepped portion of the metallic shell directly or via an intermediate member. By using the flange section as an engagement section, the plate-type detection element is axially positioned in the metallic shell. Such positioning of the plate-type detection element in the metallic shell eliminates the need for a glass seal material, thereby preventing a reduction in sensor manufacturing efficiency, which could otherwise result from employing high-temperature thermal processing.

According to the manufacturing method of the present invention, the work of assembling the flange section and the plate-type detection element is not performed simultaneously with assembling the plate-type detection element and the metallic shell, but is performed before assembling the plate-type detection element and the metallic shell.

The above practice eliminates the need to set the plate-type detection element to a predetermined angular orientation, thereby eliminating the work of setting the plate-type detection element to the predetermined angular orientation and thus facilitating attachment of the plate-type detection element to the metallic shell.

When the plate-type detection element (to which the flange section including at least the first powder-compacted ring is integrally assembled) is to be assembled to the metallic shell, the flange section engages the stepped portion, whereby the plate-type detection element can be positioned at a predetermined axial position relative to the metallic shell. Thus, by means of predetermining, in consideration of the position of the stepped portion on the metallic shell, a position on the plate-type detection element where the flange section (first powder-compacted ring) is to be attached, the plate-type detection element can be positioned at a predetermined position relative to the metallic shell. This facilitates positioning (axial positioning) of the plate-type detection element in relation to the metallic shell.

The intermediate member has a hollow portion. The hollow portion is of a sufficiently large size for the plate-type detection element to rotate about its own axis within the hollow portion. Thus, the intermediate member imposes no limitation on the angular orientation of the plate-type detection element. The intermediate member may be, for example, a packing.

In the case where an intermediate member is used, the plate-type detection element is inserted through the hollow portion of the intermediate member, and the flange section is brought into indirect contact with the stepped portion of the metallic shell via the intermediate member. Notably, use of a packing as the intermediate member enhances gastightness between the plate-type detection element and the metallic shell.

In a preferred aspect (2) of the above-described method (1) of manufacturing a sensor, the flange section further comprises a tubular protection cover covering a side surface of the first powder-compacted ring; in the first step, when the plate-type detection element is to be inserted through the element-insertion through-hole of the first powder-compacted ring, the protection cover is disposed at a position where the protection cover covers the side surface of the first powder-compacted ring; and in the second step, compressive pressure is applied to the first powder-compacted ring so as to compressively deform the first powder-compacted ring such that the cross-sectional area of the element-insertion through-hole is reduced and such that a clearance between the first powder-compacted ring and the protection cover is eliminated, whereby the flange section including the first powder-compacted ring and the protection cover is integrally assembled to the plate-type detection element.

By unitarily attaching not only the first powder-compacted ring but also the protection cover to the plate-type detection element, the flange section including the first powder-compacted ring and the protection cover serves as an engagement section of the plate-type detection element. As compared with an engagement section implemented only by the first powder-compacted ring, the engagement section that is implemented by the flange section including the first powder-compacted ring and the protection cover can exhibit enhanced strength, thereby preventing the occurrence of fracture, such as cracking or chipping, in the process of manufacturing a sensor.

In the above-described method of manufacturing a sensor, the protection cover is disposed to cover (surround) the side surface of the first powder-compacted ring. Thus, in the second step, when the first powder-compacted ring is to be compressively deformed, a jig for surrounding the side surface of the first powder-compacted ring becomes unnecessary, thereby simplifying the apparatus (equipment) for manufacturing a sensor.

In a preferred aspect (3) of the method of manufacturing a sensor in which the protection cover is used, the flange section further comprises an insulating holder located on a front-end side of the first powder-compacted ring, assuming an annular shape, and formed of an insulating material; the protection cover is formed of a metallic material, assumes a tubular shape so as to cover the side surface of the first powder-compacted ring and a side surface of the insulating holder, and has a bottom portion that abuts a front-end-portion surface of the insulating holder; the insulating holder has an insertion through-hole portion whose cross-sectional area is greater than that of the plate-type detection element as measured by sectioning in a plane perpendicular to the axial direction; the bottom portion of the protection cover has an opening portion whose cross-sectional area is greater than that of the plate-type detection element as measured by sectioning in a plane perpendicular to the axial direction; in the first step, the first powder-compacted ring and the insulating holder are covered with the protection cover such that the bottom portion of the protection cover is located on the front-end side of the insulating holder, and the plate-type detection element is inserted through the opening portion of the bottom portion of the protection cover, through the insertion through-hole portion of the insulating holder, and through the element-insertion through-hole of the first powder-compacted ring; and in the second step, axially compressive pressure is applied so as to compressively deform the first powder-compacted ring and so as to integrally assemble the flange section including the first powder-compacted ring, the insulating holder, and the protection cover to the plate-type detection element.

The protection cover having the bottom portion is integrally assembled to the plate-type detection element as a result of compressive deformation of the first powder-compacted ring and can hold the insulating holder therein by virtue of its bottom portion. Thus, when the plate-type detection element to which the flange section is integrally assembled is to be held, separation of the insulating holder from the plate-type detection element can be prevented irrespective of the orientation of the front end portion of the plate-type detection element; i.e., whether the front end portion is directed vertically (upward or downward) or horizontally (leftward or rightward).

Thus, in the process of manufacturing a sensor, when the plate-type detection element to which the flange section is integrally assembled is to be held, no limitation is imposed on the orientation of the plate-type detection element, thereby rendering manufacturing work less complicated.

The bottom portion of the protection cover can function as a packing to prevent formation of a clearance between the insulating holder and the stepped portion of the metallic shell, thereby enhancing gastightness between the plate-type detection element and the metallic shell.

Preferably, a metallic material used to form the protection cover is elastically deformable and can endure a high-temperature environment. The insulating holder is provided to prevent a powder substance used to form the first powder-compacted ring from coming out from inside the metallic shell through the through-hole of the metallic shell.

In a preferred aspect (4) of the method of manufacturing a sensor in which the protection cover having the bottom portion is used, the stepped portion of the metallic shell is formed as a taper surface tapered such that diameter increases rearward; the front-end-portion surface of the insulating holder includes at least a taper surface tapered such that diameter decreases frontward; the bottom portion of the protection cover assumes an angle different from that of the taper surface of the insulating holder at a stage before the protection cover is disposed so as to cover the first powder-compacted ring and the insulating holder; and in the second step, axially compressive pressure is applied so as to compressively deform the first powder-compacted ring and so as to deform the bottom portion of the protection cover such that the bottom portion assumes an angle substantially equal to that of the taper surface of the insulating holder, whereby the flange section is integrally assembled to the plate-type detection element.

The above method of manufacturing a sensor does not employ a practice in which the taper angle of the bottom portion of the protection cover as measured before attachment of the protection cover to the plate-type detection element is set substantially equal to the angle of the taper surface of a front end portion of the insulating holder. Instead, in the second step, the first powder-compacted ring is compressively deformed, and the bottom portion of the protection cover is deformed so as to assume an angle substantially equal to the angle of the taper surface of the front end portion of the insulating holder.

By employing a taper angle (open angle) of the taper surface of the bottom portion of the protection cover that differs, as measured before application of pressure, from the taper angle (open angle) of the front-end-portion surface of the insulating holder, even when the taper angle of the tapered front-end-portion surface of the insulating holder varies within a tolerable range, the inner tapered surface of the bottom portion of the protection cover can be favorably fitted to the tapered front-end-portion surface of the insulating holder.

Thus, even when the taper angle of the tapered front-end-portion surface of the insulating holder involves a dimensional error, the bottom portion of the protection cover can appropriately abut the insulating holder, thereby suppressing adverse effects due to dimensional errors of component members of a sensor in the process of manufacturing a sensor.

Meanwhile, in some cases, when pressure is applied to the flange portion including the first powder-compacted ring, the insulating holder and the protection cover, which are integrated with the plate-type detection element disposed in the through-hole of the metallic shell in a direction toward the front end, the protection cover may be deformed such that its transitional portion between the bottom portion and a side portion swells inward. Such a swollen portion of the protection cover may impose inappropriate pressure on the insulating holder, potentially resulting in fracture of the insulating holder.

In a preferred aspect (5) as applied to (3) and (4) above, in order to avoid the above problem, the insulating holder is formed such that, when the insulating holder is disposed in the protection cover, a clearance is formed between the insulating holder and the inner surface of the transitional corner portion of the protection cover, the transitional corner portion being at a junction of the bottom portion and the side portion.

That is, even when the transitional corner portion, located between the bottom portion and the side portion, of the protection cover swells inward, use of the insulating holder assuming the above-mentioned form prevents contact between the swollen portion and the insulating holder, thereby preventing fracture of the insulating holder.

The thus-formed insulating holder is configured, for example, such that in addition to the taper surface (hereinafter also referred to as a first taper surface) whose diameter decreases frontward and which is engaged with the bottom portion of the protection cover, a second taper surface is formed on the front end portion of the insulating holder to surround the first taper surface. The taper angle of the second taper surface is set different from the taper angle of the first taper surface so as to form a clearance between the second taper surface and the inner surface of the protection cover.

The method of manufacturing a sensor in which the thus-formed insulating holder is used enhances the efficiency of manufacturing a sensor, since fracture of the insulating holder, which could otherwise result from swelling deformation of the protection cover, can be prevented to thereby lower the incidence of a defective sensor.

In a preferred aspect of (6) of the above-described method of manufacturing a sensor as applied to (2), (3) and (4) above, the sensor further comprises a protector section formed so as to cover the front end portion of the plate-type detection element at which the detection portion is formed; the protection cover has a cover-side engagement portion for engaging the stepped portion of the metallic shell and is formed integrally with the protector section; and in the first step, the protection cover formed integrally with the protector section is caused to cover the side surface of the first powder-compacted ring, and the protector section is caused to cover the detection portion of the plate-type detection element.

The above method of manufacturing a sensor can simultaneously achieve, in a single operation, disposition of the protection cover at a position covering the side surface of the first powder-compacted ring and disposition of the protector section at a position covering the detection portion of the plate-type detection element. As compared with the case where the protection cover and the protector section are individually formed, the number of working steps in the process of manufacturing a sensor can be reduced.

Since, at an intermediate stage of manufacturing a sensor, the plate-type detection element is covered and protected with the protector section, fracture of the plate-type detection element can be prevented in the subsequent course of manufacture. Particularly, when the plate-type detection element is to be disposed in the through-hole of the metallic shell, accidental contact between the plate-type detection element and the metallic shell can be prevented. Therefore, the work of attaching the plate-type detection element to the metallic shell does not require special attention to avoid contact between the plate-type detection element and the metallic shell, thereby rendering the attachment work less complicated.

Furthermore, integral formation of the protection cover and the protector section reduces the number of component members of a sensor, thereby reducing manufacturing cost.

In a preferred aspect (7) as applied to (1) to (5) of the above-described method of manufacturing a sensor, the plate-type detection element has a protection layer formed at least on a surface of an electrode of the front end portion, the surface of the electrode being exposed to an object to be measured; and in the first step, the plate-type detection element is inserted through the element-insertion through-hole of the first powder-compacted ring such that the rear end portion of the plate-type detection element serves as a leading portion.

According to the above-described method of manufacturing a sensor, in the first step, the plate-type detection element is inserted through the element-insertion through-hole of the first powder-compacted ring such that the rear end portion of the plate-type detection element serves as a leading portion. Thus, the work of inserting through the first powder-compacted ring is free from a problem of the first powder-compacted ring scraping the protection layer from the front end portion of the plate-type detection element.

Thus, the method of the present invention does not require attention to prevention of exfoliation of the protection layer in the process of unitarily attaching the flange section including the first powder-compacted ring to the plate-type detection element having the protection layer, thereby rendering work in the process of manufacturing a sensor less complicated.

In a preferred aspect (8) as applied to (1) to (6) of the above-described method of manufacturing a sensor, the sensor further comprises a filler member formed by compacting a powder substance into an annular shape, and disposed so as to surround a portion of the plate-type detection element located on the rear-end side of the flange section; in the third step, the plate-type detection element is disposed in the through-hole of the metallic shell such that the filler member is disposed around the portion of the plate-type detection element located on the rear-end side of the flange section; and after the third step is performed, pressure directed toward the stepped portion of the metallic shell is applied to the filler member so as to fill a space between the plate-type detection element and the metallic shell with the filler member, whereby the filler member establishes gastight sealing between the plate-type detection element and the metallic shell.

According to the above method of manufacturing a sensor, in the third step subsequent to the second step in which the flange section is integrally assembled to the plate-type detection element, the annular filler member is fitted to the plate-type detection element, whereby the filler member can be supported by the flange section. In other words, the filler member is fitted from above to the plate-type detection element whose front end faces downward, such that the rear end of the plate-type detection element serves as a leading end and is inserted through the filler member. As a result, the filler member is disposed around the plate-type detection element while resting on the flange section.

In the case where, at a stage before disposing the plate-type detection element in the through-hole of the metallic shell, the filler member is disposed around the plate-type detection element as described above, the position of the filler member in relation to the plate-type detection member can be readily checked, so that the filler member can be disposed in an appropriate condition.

In the case where, after the plate-type detection element is disposed in the through-hole of the metallic shell, the filler member is inserted into and disposed in the through-hole, the disposed condition of the filler member is difficult to check, because of difficulty in visually checking the interior of the through-hole of the metallic shell, and the disposed condition of the filler member is difficult to modify, because of narrow space. As a result, the filler member may be disposed in an inappropriate condition (e.g., the filler member may be disposed in a tilted condition). By contrast, the method of manufacturing a sensor of the present invention can readily dispose the filler member in an appropriate condition in relation to the plate-type detection element, thereby rendering sensor assembly work less complicated.

Also, in the case where, after the plate-type detection element is disposed in the through-hole of the metallic shell, the filler member is inserted into and disposed in the through-hole, a certain structure of the metallic shell causes the filler member to drop a rather long distance, such that the impact thereof may fracture the filler member.

By contrast, in the case of the method of manufacturing a sensor of the present invention, the filler member can be disposed around the plate-type detection element before the plate-type detection element is disposed in the through-hole of the metallic shell, thereby preventing fracture of the filler member, which could otherwise result from the impact of the drop. In other words, the filler member is disposed around the plate-type detection element while resting on the flange section; and then, the plate-type detection element is held at a rear end portion thereof and is disposed, together with the filler member, in the through-hole of the metallic shell. Thus, the occurrence of drop impact can be prevented, thereby preventing fracture of the filler member.

Furthermore, since the filler member is caused to fill under pressure the space between the plate-type detection element and the metallic shell, the plate-type detection element and the metallic shell are assembled in a more strengthened condition, and good gastight sealing can be established therebetween.

Figure 1:
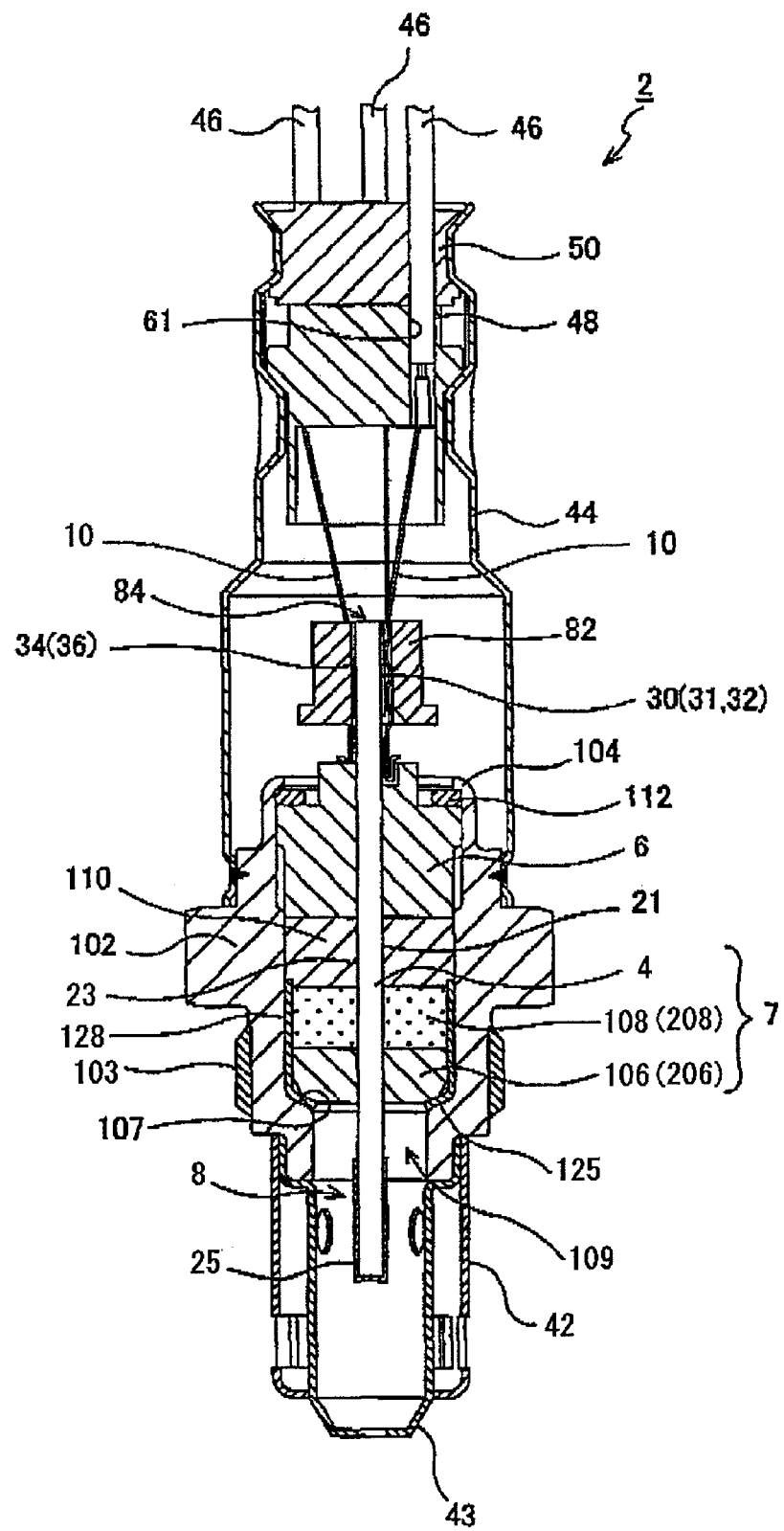
FIG. 1 is a sectional view showing the overall configuration of an air-fuel ratio sensor according to an embodiment of the invention.

Reference numerals are used to define elements shown in the drawings as follows.

2 . . . full-range air-fuel ratio sensor
4 . . . detection element
8 . . . detection portion
30, 31, 32, 34, 36 . . . electrode terminal portion
102 . . . metallic shell
106 . . . ceramic holder
107 . . . stepped portion
108 . . . first powder layer
109 . . . through-hole
110 . . . second powder layer
125 . . . protection cover
126 . . . bottom portion
160 . . . second full-range air-fuel ratio sensor
161 . . . second protection cover
162 . . . cover portion
163 . . . protector portion
164 . . . cover-side engagement portion
200 . . . third full-range air-fuel ratio sensor
206 . . . second ceramic holder
208 . . . first powder-compacted ring
210 . . . second powder-compacted ring

DETAILED DESCRIPTION OF THE PREFERRED EMBODIMENTS

Various embodiments of the present invention will next be described in detail with reference to the drawings. However, the present invention should not be construed as being limited thereof.

A first embodiment is of a full-range air-fuel ratio sensor 2 (hereinafter also referred to as air-fuel ratio sensor 2), which is a type of gas sensor. For use in air-fuel ratio feedback control in various internal combustion engines including those of cars, the air-fuel ratio sensor 2 includes a detection element (gas sensor element) for detecting a specific gas, or an object to be measured, contained in exhaust gas and is mounted in an exhaust pipe of an internal combustion engine.

FIG. 1 is a sectional view showing the overall configuration of the air-fuel ratio sensor 2, which is embodied through application of the method of the present invention.

The air-fuel ratio sensor 2 includes a tubular metallic shell 102 having a male threaded portion 103 formed on the outer surface thereof, the male threaded portion 103 being adapted to fixedly attach the air-fuel ratio sensor 2 to an exhaust pipe; a detection element 4 assuming the shape of an axially (in FIG. 1, vertically) extending plate; a tubular ceramic sleeve 6 surrounding the detection element 4 from all radial directions; an insulating contact member 82 disposed such that the wall surface of a contact insertion through-hole 84, which axially extends through the insulating contact member 82, surrounds a rear end portion of the detection element 4; and five lead frames 10 disposed between the detection element 4 and the insulating contact member 82.

The detection element 4 assumes the shape of an axially extending plate and is configured as follows: a detection portion 8 covered with a protection layer 25 is formed at a front end portion thereof (in FIG. 1, at a lower end portion) directed to a gas to be measured; and electrode terminal portions 30, 31, 32, 34, and 36 are formed on a first plate surface 21 and on a second plate surface 23, which are opposite sides of a rear end portion thereof (in FIG. 1, an upper end portion). The lead frames 10 are disposed between the detection element 4 and the insulating contact member 82 to thereby electrically connect to the corresponding electrode terminal portions 30, 31, 32, 34, and 36 of the detection element 4. The lead frames 10 are also electrically connected to corresponding lead wires 46, which extend between the interior and the exterior of the sensor, thereby forming current paths through which current flows between external equipment, to which the lead wires 46 are connected, and the electrode terminal portions 30, 31, 32, 34, and 36.

The metallic shell 102 assumes a substantially tubular shape and has an axially extending through-hole 109, which has a circular cross section as sectioned perpendicularly to the axial direction. A stepped portion 107 projects radially inward from the wall of the through-hole 109. The metallic shell 102 holds the detection element 4 that extends through the through-hole 109 such that the detection portion 8 is located on the frontward outside of the through-hole 109, whereas the electrode terminal portions 30, 31, 32, 34, and 36 are located on the rearward outside of the through-hole 109. The stepped portion 107 has a taper surface that is inclined in relation to a plane perpendicular to the axial direction. The taper surface faces rearward, and its diameter increases rearward.

In the through-hole 109 of the metallic shell 102, an annular ceramic holder 106, a first powder layer 108, a second powder layer 110, and the ceramic sleeve 6, from the front side to the rear side, are arranged in layers so as to surround the detection element 4 from all radial directions. The first powder layer 108 is attached to the detection element 4 before the detection element 4 is inserted into the metallic shell 102, whereas the second powder layer 110 is charged into a space between the detection element 4 and the metallic shell 102 after the detection element 4 is inserted into the metallic shell 102. A crimp ring 112 is disposed between the ceramic sleeve 6 and a rear end portion 104 of the metallic shell 102. The rear end portion 104 of the metallic shell 102 is crimped so as to press the ceramic sleeve 6 frontward via the crimp ring 112.

Figure 2:
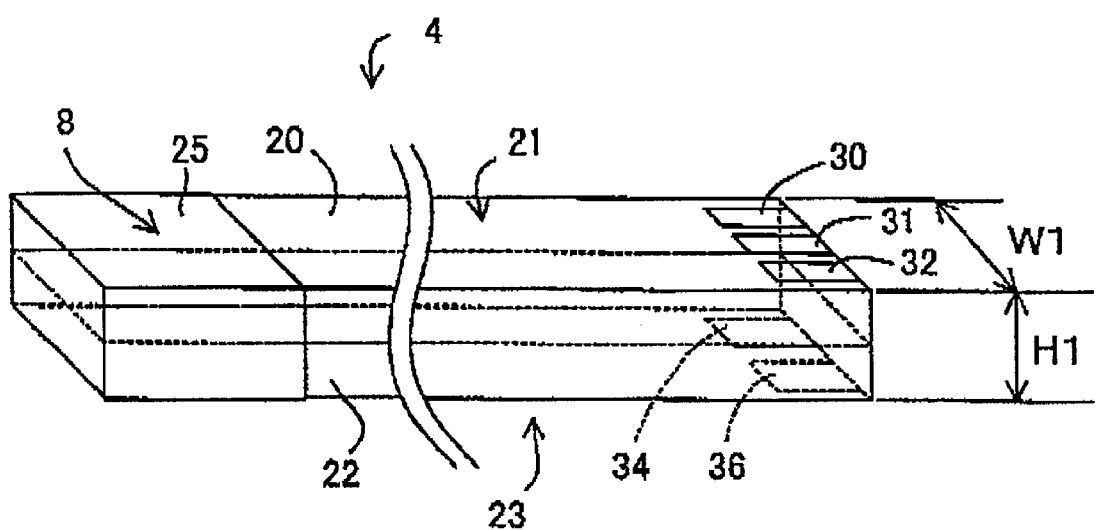
FIG. 2 is a perspective view showing the schematic structure of a detection element.

FIG. 2 is a perspective view showing the schematic structure of the detection element 4. In FIG. 2, an axially intermediate portion of the detection element 4 is omitted.

The detection element 4 is formed into a plate shape having a rectangular cross section such that an element portion 20 formed into the shape of an axially (in FIG. 2, horizontally) extending plate and a heater 22 formed in the shape of an axially extending plate are laminated. Since the detection element 4 used in the air-fuel ratio sensor 2 is publicly known, detailed description of its internal structure is omitted. Only schematic configuration of the detection element 4 will be described below.

The element portion 20 includes an oxygen concentration cell element configured such that porous electrodes are formed on corresponding opposite sides of a solid electrolyte substrate; an oxygen pump element configured such that porous electrodes are formed on corresponding opposite sides of a solid electrolyte substrate; and a spacer sandwiched between the oxygen concentration cell element and the oxygen pump element and adapted to form a hollow measurement gas chamber. The solid electrolyte substrates are formed of solid solution of zirconia that contains yttria as a stabilizer. The porous electrodes are formed predominantly of Pt. The spacer used to form a measurement gas chamber is formed predominantly of alumina and is disposed such that one porous electrode of the oxygen concentration cell element and one porous electrode of the oxygen pump element are exposed to the interior of the hollow measurement gas chamber. The measurement gas chamber is located at a position corresponding to a front end portion of the element portion 20. A diffusion-controlling portion formed of porous ceramic is located at a front end portion of the spacer, in order to establish communication between the measurement gas chamber and the exterior of the detection element 4. A portion of the detection element 4 at which the measurement gas chamber is formed corresponds to the detection portion 8.

The heater 22 is configured such that a heating resistor pattern formed predominantly of Pt is sandwiched between insulating substrates formed predominantly of alumina.

The element portion 20 and the heater 22 are joined via a ceramic layer (e.g., zirconia ceramic or alumina ceramic). A poisoning resistant protection layer 25 formed of porous ceramic is formed at least on the surfaces of electrodes provided at a front end portion of the detection element 4, the electrode being exposed to an object to be measured (in the present embodiment, exhaust gas). Notably, in the present embodiment, the protection layer 25 covers the entire surface of a front end portion of the detection element 4 including the surfaces of the electrodes.

As shown in FIG. 2, in the detection element 4, the three electrode terminal portions 30, 31, and 32 are formed on a rear end portion (in FIG. 2, a right end portion) of the first plate surface 21, and the two electrode terminal portions 34 and 36 are formed on a rear end portion of the second plate surface 23. The electrode terminal portions 30, 31, and 32 are formed on the element portion 20. One of the electrode terminal portions 30, 31, and 32 is electrically connected, in common, to one porous electrode of the oxygen concentration cell element exposed to the interior of the measurement gas chamber and to one porous electrode of the oxygen pump element exposed to the interior of the measurement gas chamber. The remaining two of the electrode terminal portions 30, 31, and 32 are electrically connected to the other porous electrode of the oxygen concentration cell element and to the other porous electrode of the oxygen pump element, respectively. The electrode terminal portions 34 and 36 are formed on the heater 22 and connected to corresponding opposite ends of the heating resistor pattern via corresponding vias (not shown) extending in the thickness direction of the heater.

The detection element 4 has a width W1 of 4.2 [mm] and a height H1 of 1.3 [mm].

As shown in FIG. 1, the thus-configured detection element 4 is fixed in the metallic shell 102, which is fixed to an exhaust pipe, such that the frontward (in FIG. 1, lower) detection portion 8 projects from the front end of the metallic shell 102, whereas the rearward electrode terminal portions 30, 31, 32, 34, and 36 project from the rear end of the metallic shell 102.

As shown in FIG. 1, a double protector consisting of an outer protector 42 and an inner protector 43 is attached, by means of welding or the like, to the outer circumference of a front end portion (in FIG. 1, a lower end portion) of the metallic shell 102 while covering a projecting portion of the detection element 4. The outer and inner protectors 42 and 43 have a plurality of hole portions and are formed of metal (e.g., stainless steel).

A sleeve 44 is fixed to the outer circumference of a rear end portion of the metallic shell 102. A ceramic separator 48 and a grommet 50 are disposed in a rearward (in FIG. 1, upper) opening portion of the sleeve 44. The ceramic separator 48 has five lead wire insertion through-holes 61 through which corresponding lead wires 46 are inserted and connected to the corresponding electrode terminal portions 30, 31, 32, 34, and 36 of the detection element 4.

The insulating contact member 82 is disposed on a rear end portion (in FIG. 1, an upper end portion) of the detection element 4, which rear end portion projects from the rear end portion 104 of the metallic shell 102. The insulating contact member 82 is disposed around the electrode terminal portions 30, 31, 32, 34, and 36 formed on the surface of a rear end portion of the detection element 4.

Figure 3A:
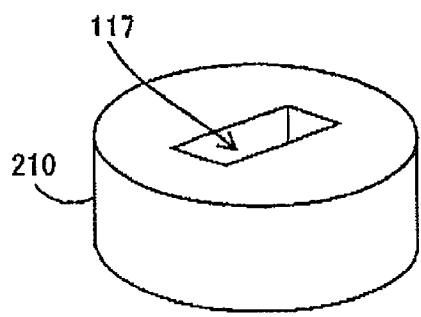
FIGS. 3(a)-3(c) are a series of perspective views of a ceramic holder, a first powder-compacted ring, and a second powder-compacted ring as viewed before attachment to the detection element.
Figure 3B:
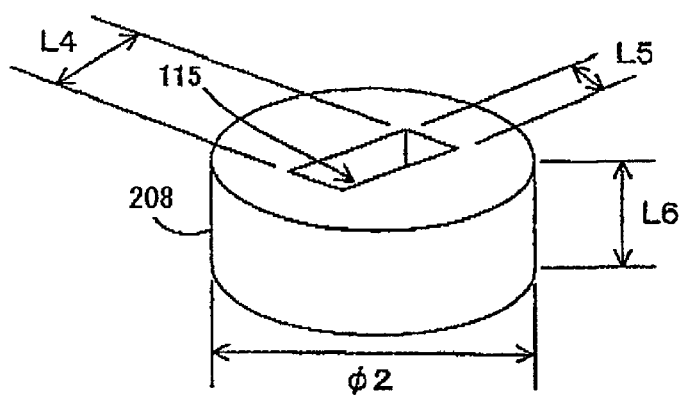
Figure 3C:
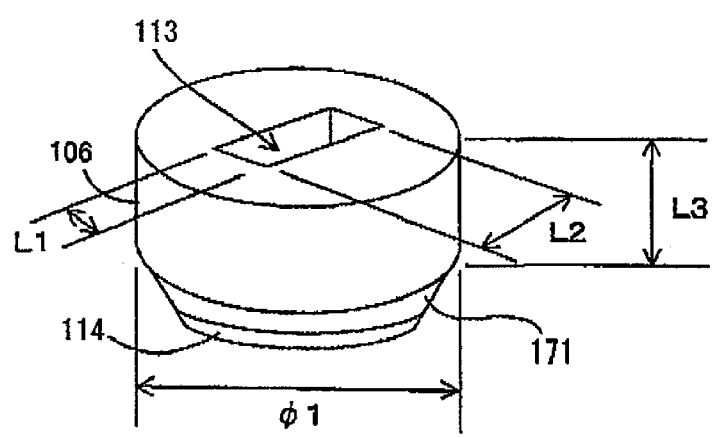

Next will be described the ceramic holder 106 formed of an insulating material, the first powder layer 108 formed of talc powder, and the second powder layer 110 formed of talc powder. FIGS. 3(a)-3(c) are a series of perspective views of the ceramic holder 106, a first powder-compact ring 208 that is to become the first powder layer 108, and a second powder-compact ring 210 that is to become the second powder layer 110 before being assembled to the detection element 4. In representing the members in FIGS. 3(a)-3(c), the lower side corresponds to the front-end side, and the upper side corresponds to the rear-end side.

The ceramic holder 106 is formed into an annular shape having an axially extending insertion through-hole portion 113. A front-end taper surface 114 of a front end portion of the ceramic holder 106 is formed such that its diameter decreases frontward. The front-end taper surface 114 engages the stepped portion 107 of the metallic shell 102 via a protection cover, which will be described below.

The ceramic holder 106 has an outside diameter [mm] and a height L3 of 3.6 [mm]. The insertion through-hole portion 113 has a short-side length L1 of 1.6 [mm] and a long-side length L2 of 4.5 [mm].

Figure 6:
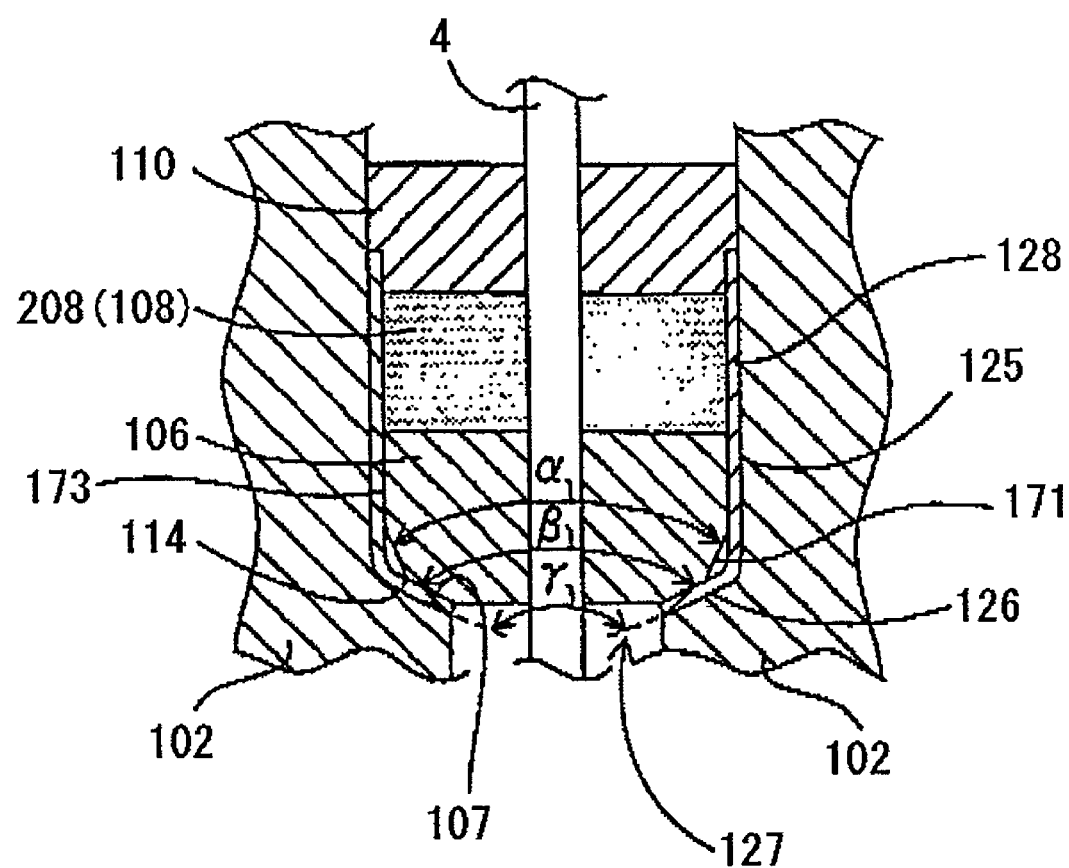
FIG. 6 is an enlarged sectional view showing a portion of the air-fuel ratio sensor at which the ceramic holder is disposed.

FIG. 6 is an enlarged sectional view showing a portion of the air-fuel ratio sensor 2 at which the ceramic holder 106 is disposed.

As shown in FIG. 6, an open angle β [degree] of the front-end taper surface 114 of the ceramic holder 106 is substantially equal to an open angle γ [degree] of the taper surface of the stepped portion 107 of the metallic shell 102. As shown in FIG. 6, the ceramic holder 106 has a second taper surface 171 formed between its side surface 173 and the front-end taper surface 114. As shown in FIG. 6, on a section of the ceramic holder 106 taken by a plane that includes the sensor axis, the front-end taper surface 114 and the second taper surface 171 are formed such that an open angle α [degree] of the second taper surface 171 and the open angle β [degree] of the front-end taper surface 114 establish the relation "α<β." In the present embodiment, α=110 [degrees] and β=120 [degrees].

Referring back to FIGS. 3(a)-3(c), on comparison at a stage before insertion of the detection element 4 through the insertion through-hole portion 113, the cross-sectional area of the insertion through-hole portion 113 of the ceramic holder 106 is slightly greater than that of the detection element 4 as measured by sectioning by a plane perpendicular to the axial direction; i.e., the insertion through-hole portion 113 of the ceramic holder 106 has a sufficiently large size for allowing insertion of the detection element 4 therethrough. The ceramic holder 106 is provided to prevent talc powder used to form the first powder-compacted ring 208 from dropping out from inside the metallic shell 102 through the through-hole 109 of the metallic shell 102.

The first powder-compacted ring 208 is formed by compacting talc powder and is formed into an annular shape having an axially extending element-insertion through-hole 115. The cross-sectional area of the element-insertion through-hole 115 of the first powder-compacted ring 208 is slightly greater than that of the detection element 4 as measured by sectioning by a plane perpendicular to the axial direction; i.e., the element-insertion through-hole 115 of the first powder-compacted ring 208 has a sufficiently large size for allowing insertion of the detection element 4 therethrough.

The first powder-compacted ring 208 has an outside diameter φ2 of 10.46 [mm] and a height L6 of 4.0 [mm]. The element-insertion through-hole 115 has a short-side length L5 of 1.7 [mm] and a long-side length L4 of 4.5 [mm].

The second powder-compacted layer 210 is formed by compacting talc powder and is formed into an annular shape having an axially extending second element-insertion through-hole 117. The cross-sectional area of the second element-insertion through-hole 117 of the second powder-compacted ring 210 is slightly greater than that of the detection element 4 as measured by sectioning by a plane perpendicular to the axial direction; i.e., the second element-insertion through-hole 117 of the second powder-compacted ring 210 has a sufficiently large size for allowing insertion of the detection element 4 therethrough.

In manufacturing the first powder-compacted ring 208 and the second powder-compacted ring 210, use of, for example, water glass as a binder enables compaction of talc power into a predetermined shape.

The second powder layer 110 can be formed as follows: a talc powder is previously formed into an annular powder-compacted ring (second powder-compacted ring 210); the powder-compacted ring is disposed to fill a space between the metallic shell 102 and the detection element 4; and then pressure is axially applied to the powder-compacted ring such that the powder-compacted ring is re-formed into the second powder layer 110. Use of the previously formed powder-compacted ring facilitates the work of forming the second powder layer.

Figure 4:
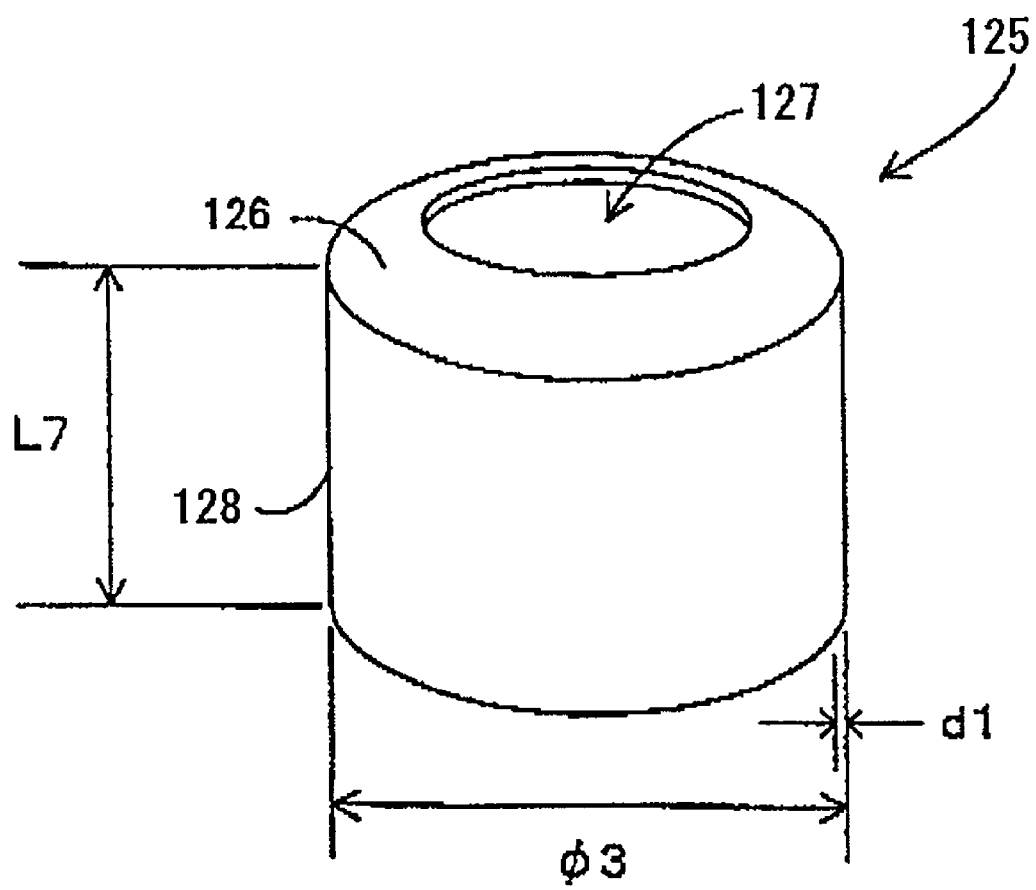
FIG. 4 is a perspective view of a protection cover.
Figure 5:
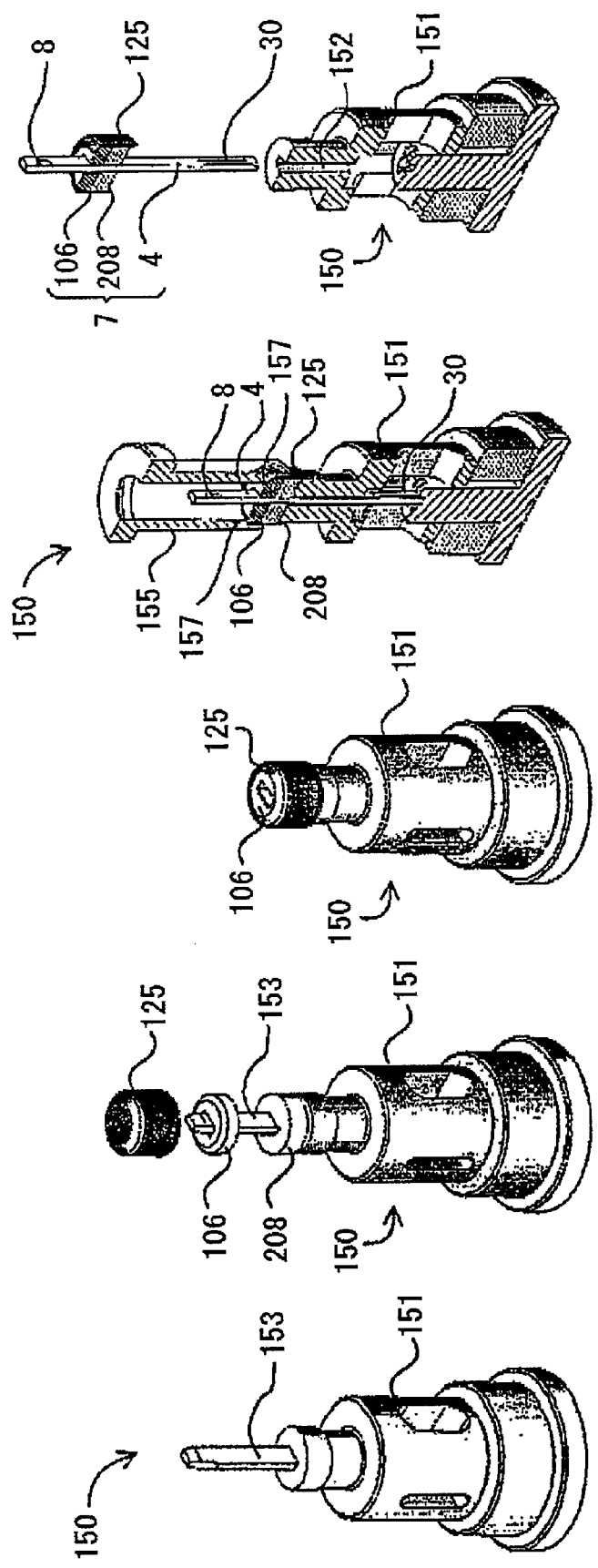
FIGS. 5(a)-5(e) are a series of explanatory views showing the steps of fabricating an element unit by use of an element unit fabrication jig.

Next, a protection cover 125 will be described. FIG. 4 is a perspective view of the protection cover 125. In representation of the protection cover 125 in FIG. 4, the upper side corresponds to the front-end side, and the lower side corresponds to the rear-end side.

The protection cover 125 is formed of a metallic material (e.g., stainless steel) and formed into a tubular shape whose size is sufficiently large to accommodate the ceramic holder 106 and the first powder-compacted ring 208. A bottom portion 126 is formed at a front end portion of the protection cover 125 and abuts the front-end taper surface 114 of the ceramic holder 106 after attachment to the metallic shell 102. In other words, the protection cover 125 is formed into such a tubular shape covering the side surface of the ceramic holder 106, the side surface of the first powder-compacted ring 208, and a front end portion of the ceramic holder 106.

At a stage before the first powder-compacted ring 208 is compressed to thereby be integrally assembled to the detection element 4 while filling a space in the protection cover 125, the bottom portion 126 of the protection cover 125 assumes a taper shape whose taper angle differs from the taper angle of the stepped portion 107 of the metallic shell 102, which will be described in detail below. The bottom portion 126 of the protection cover 125 has an opening portion 127, which axially extends through the bottom portion 126. The cross-sectional area of the opening portion 127 is greater than that of the detection element 4 as measured by sectioning by a plane perpendicular to the axial direction. The hollow portion 127 has a sufficiently large size such that the detection element 4 inserted therethrough can be rotated around its own axis.

The protection cover 125 has an outside diameter φ3 of 11.43 [mm], a height L7 of 8.5 [mm], and a thickness d1 of 0.4 [mm].

Next, fabrication of an element unit 7 will be described. The element unit 7 is formed by means of unitarily attaching the ceramic holder 106, the first powder-compacted ring 208, and the protection cover 125 to the detection element 4. FIGS. 5(a)-5(d) are a series of explanatory views showing steps of fabricating the element unit 7 by use of an element unit fabrication jig 150.

In the present embodiment, before fabricating the element unit 7, the detection element 4 (see FIG. 2), including a protection layer 25 formed on the surface of a front-end portion thereof, is prepared.

The element unit fabrication jig 150 includes a pedestal 151 having an element rest portion 152 for accommodating a rear end portion of the detection element 4; a pin member 153 whose cross-sectional shape is substantially similar to that of the detection element 4; and a pressure application member 155 for applying pressure along the axial direction of the detection element 4 to compressively deform the first powder-compacted ring 208.

As shown in FIGS. 5(a)-5(d), in the first step of fabricating the element unit 7, the pin member 153 is inserted into the element rest portion 152 of the pedestal 151. In the second step, the first powder-compacted ring 208 and then the ceramic holder 106 are fitted to the pin member 153; subsequently, the protection cover 125 is disposed so as to cover the first powder-compacted ring 208 and the ceramic holder 106.

In the third step, the pin member 153 is pulled out. As a result, the protection cover 125, the ceramic holder 106, and the first powder-compacted ring 208 are arranged in layers on the pedestal 151.

In the fourth step, the detection element 4 is inserted through the opening portion 127 of the protection cover 125, through the insertion through-hole portion 113 of the ceramic holder 106, through the element-insertion through-hole 115 of the first powder-compacted ring 208, and into the element rest portion 152 so that the rear end (corresponding to a rear end portion at which the electrode terminal portion 30 is formed) of the detection element 4 serves as a leading end. The detection element 4 engages an interior portion of the pedestal 151, whereby the position of the first powder-compacted ring 208 is determined in relation to the detection element 4.

As described above, in the fourth step, the detection element 4 is inserted through the insertion through-hole portion 113 of the ceramic holder 106, the element-insertion through-hole 115 of the first powder-compacted ring 208, etc., such that the rear end of the detection element 4 serves as a leading end; thus, exfoliation of the protection layer 25 formed on the front end portion of the detection element 4, which could otherwise result from the inserting work, can be effectively suppressed.

Dimensions of the pedestal 151, such as the depth of the element rest portion 152, are appropriately set such that the relative position between the detection element 4 and the first powder-compacted ring 208 as established by the inserting work using the pedestal 151 becomes the relative position between the detection element 4 and the first powder-compacted ring 208 as established at the time of completion of the air-fuel ratio sensor 2.

Subsequently, pressure directed toward the pedestal 151 is applied to the ceramic holder 106 via the protection cover 125 by means of the pressure application member 155, thereby applying an axially compressive pressure to the first powder-compacted ring 208. An abutment surface 157 of the pressure application member 155 abuts the protection cover 125 to thereby apply pressure to the first powder-compacted ring 208. The abutment surface 157 is tapered and has an open angle β (see FIG. 6) substantially equal to that of the front-end taper surface 114 of the ceramic holder 106. In other words, the open angle of the abutment surface 157 of the pressure application member 155 is adjusted beforehand to a value substantially equal to the open angle γ (see FIG. 6) of the stepped portion 107 of the metallic shell 102. As a result of the pressure application member 155 applying compressive pressure to the first powder-compacted ring 208, the first powder-compacted ring 208 is compressed and deformed such that the cross-sectional area of the element insertion hole 115 is reduced, whereby the first powder-compacted ring 208 is integrally assembled to the detection element 4. Also, the first powder-compacted ring 208 is compressed and deformed such that the side surface of the first powder-compacted ring 208 comes into close contact with the inner circumferential surface of the protection cover 125, whereby the protection cover 125 and the ceramic holder 106, together with the first powder-compacted ring 208, are integrally assembled to the detection element 4.

The bottom portion 126 of the protection cover 125 is formed beforehand into a taper shape. However, the open angle of the bottom portion 126 as measured before application of pressure by means of the pressure application member 155 (in other words, before the fourth step) is set different from the open angle β of the front-end taper surface 114 of the ceramic holder 106. By means of employing an open angle of the bottom portion 126 of the protection cover 125 that differs, as measured before application of pressure, from the open angle β of the front-end taper surface 114 of the ceramic holder 106, even when the open angle β of the ceramic holder 106 varies within a tolerable range, the inner tapered surface of the bottom portion 126 can be favorably fitted to the front-end taper surface 114 of the ceramic holder 106 at the time of application of pressure.

In the fifth step, the element unit 7, which is an assembly of the first powder-compacted ring 208, the ceramic holder 106, the protection cover 125, and the detection element 4, is removed from the pedestal 151, whereby the element unit 7 is completed.

Next, the work of unitarily attaching the thus-assembled element unit 7 (an assembly of the first powder-compacted ring 208, the ceramic holder 106, the protection cover 125, and the detection element 4) to the metallic shell 102 will be described.

First, the second powder-compacted ring 210 is fitted to a rear end portion of the detection element 4 of the element unit 7 and is then moved frontward so as to rest on the rear-end side of the first powder-compacted ring 208. Then, the element unit 7 (an assembly of the first powder-compacted ring 208, the ceramic holder 106, the protection cover 125, and the detection element 4), together with the second powder-compacted ring 210, is inserted into the through-hole 109 of the metallic shell 102 such that the front end of the detection element 4 serves as a leading end.

At this time, the metallic shell 102 is arranged with its front end facing downward. While the detection element 4 is held at a rear end portion located rearward of the second powder-compacted ring 210, the element unit 7 is lowered until the bottom portion 126 of the protection cover 125 abuts the stepped portion 107 of the metallic shell 102. In this manner, the element unit 7 can be inserted into the through-hole 109.

The above insertion work causes the bottom portion 126 of the protection cover 125 to engage the stepped portion 107 of the metallic shell 102, whereby the element unit 7 is axially positioned in the metallic shell 102. In other words, the first powder-compacted ring 208 engages the stepped portion 107 of the metallic shell 102 via the ceramic holder 106 and the protection cover 125, whereby the detection element 4 is axially positioned in the metallic shell 102.

Next, the ceramic sleeve 6 is fitted to a rear end portion of the detection element 4 disposed in the metallic shell 102; and the second powder-compacted ring 210, the ceramic sleeve 6, and the crimp ring 112 are arranged in layers on the rear-end side of the first powder-compacted ring 208. Subsequently, the rear end portion 104 of the metallic shell 102 is crimped so as to press the ceramic sleeve 6 frontward via the crimp ring 112.

By means of the above crimping work, pressure directed toward the stepped portion 107 (axially compressive pressure) is applied to the second powder-compacted ring 210, whereby the second powder-compacted ring 210 is compressively deformed to thereby unitarily attach the detection element 4 (element unit 7) to the metallic shell 102 as shown in FIG. 1.

In the work of crimping the rear end portion 104 of the metallic shell 102, the bottom portion 126 of the protection cover 125 is sandwiched between the ceramic holder 106 and the stepped portion 107, thereby establishing gastightness between the stepped portion 107 and the ceramic holder 106.

Meanwhile, when the above-described crimping work causes pressure to be applied axially frontward to the second powder-compacted ring 210, pressure is also applied axially frontward to the bottom portion 126 of the protection cover 125 of the element unit 7. Accordingly, depending on the magnitude of the applied pressure, a peripheral portion of the bottom portion 126 may swell inward, potentially causing cracking of the ceramic holder 106. However, referring to FIG. 6, in the present embodiment, the ceramic holder 106 has the second taper surface 171 having an open angle $\alpha$ smaller than the open angle $\beta$ of the front-end taper surface 114, thereby forming a clearance between the second taper surface 171 and the inner circumferential surface of the protection cover 125. Thus, even when the peripheral portion of the bottom portion 126 swells inward as a result of the second powder-compacted ring 210 being compressed while the element unit 7 engages the stepped portion 107 of the metallic shell 102, the swollen portion becomes unlikely to contact the ceramic holder 106 (second taper surface 171), thereby effectively suppressing the above-mentioned occurrence of cracking.

Figure 7:
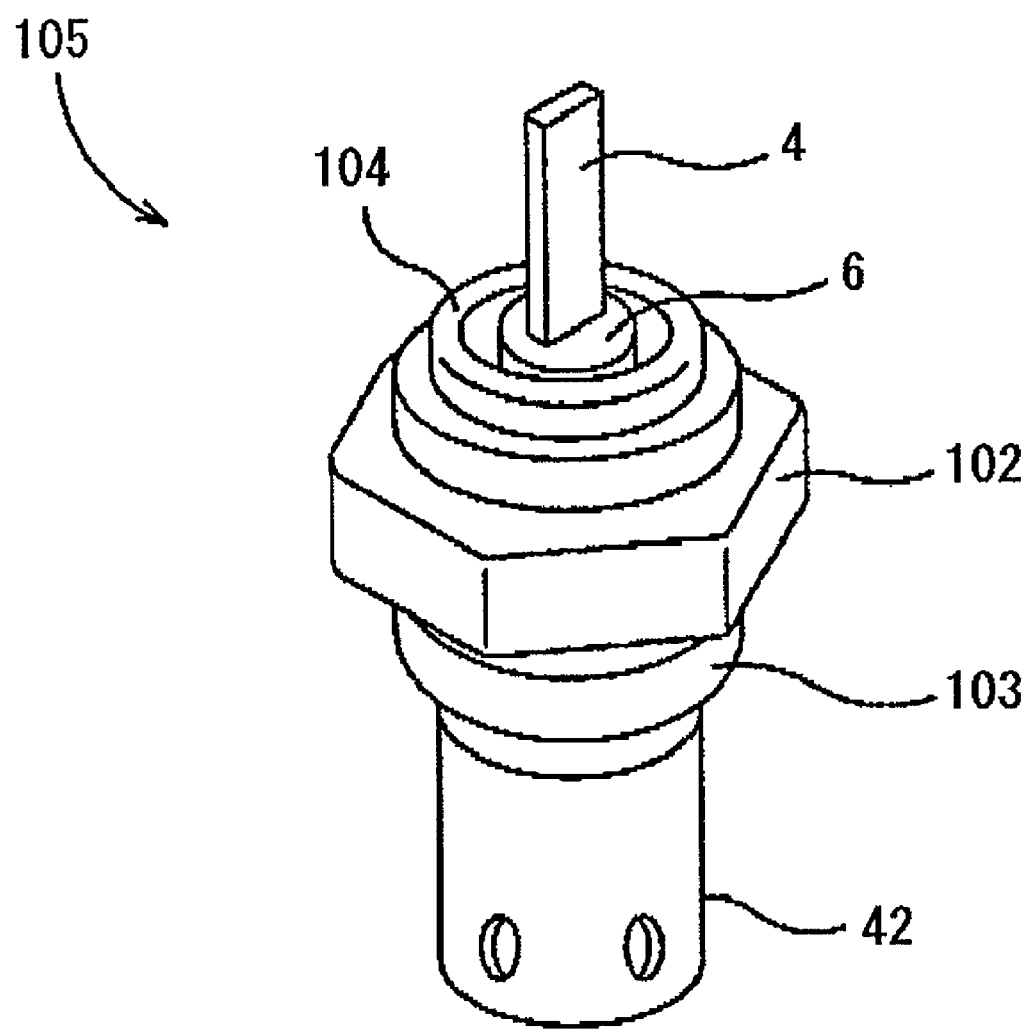
FIG. 7 is a perspective view of an intermediate assembly obtained by integrally assembling the detection element and other members, such as the first powder-compacted ring and a metallic shell.

Assembling of the element unit 7 and other members, such as the ceramic sleeve 6 and the metallic shell 102, yields an intermediate assembly 105. FIG. 7 is a perspective view of the intermediate assembly 105. FIG. 7 shows the intermediate assembly 105 including the outer protector 42.

Attachment of various members, such as the lead frames 10, the insulating contact member 82, and the sleeve 44, to the intermediate assembly 105 yields the air-fuel ratio sensor 2 shown in FIG. 1.

Correspondence between components appearing in the present embodiment and those appearing in the claims appended hereto is as follows: the detection element 4 corresponds to the plate-type detection element; first powder-compacted ring 208 corresponds to the powder-compacted ring; the ceramic holder 106 corresponds to the insulating holder; an assembly of the first powder layer 108 (first powder-compacted ring 208), the ceramic holder 106, and the protection cover 125 corresponds to the flange section; and the second powder layer 110 corresponds to the filler member.

Correspondence between the steps of present embodiment and the claims appended hereto is as follows: the step of inserting the detection element 4 through the protection cover 125, through the ceramic holder 106, and through the first powder-compacted ring 208 as shown in FIG. 5(d) of fabricating the element unit 7 corresponds to the first step; the step of applying axially compressive pressure to the first powder-compacted ring 208 by means of the pressure application member 155 as shown in FIG. 5(d) of fabricating the element unit 7 corresponds to the second step; and the step of inserting the element unit 7 into the through-hole 109 of the metallic shell 102 to thereby engage the first powder-compacted ring 208 with the stepped portion 107 via the bottom portion 126 of the protection cover 125 and the ceramic holder 106 corresponds to the third step.

According to the above-described method of manufacturing the air-fuel ratio sensor 2, in a fourth step of fabricating the element unit 7, the detection element 4 is inserted through the opening portion 127 of the protection cover 125, through the insertion through-hole portion 113 of the ceramic holder 106, and through the element-insertion through-hole 115 of the first powder-compacted ring 208 such that the rear end (corresponding to a rear end portion at which the electrode terminal portion 30 is formed) of the detection element 4 serves as a leading end. Thus, in inserting the detection element 4, the protection layer 25 formed on the front end portion of the detection element 4 is not scraped by the protection cover 125, the ceramic holder 106, or the first powder-compacted ring 208.

Thus, in the process of manufacturing a sensor, when the protection cover 125, the ceramic holder 106, and the first powder-compacted ring 208 are integrally assembled to the detection element 4 in order to form on the detection element 4 an engagement section to engage the stepped portion 107 of the metallic shell 102, occurrence of exfoliation of the protection layer 25 can be prevented.

In the fourth step, pressure is applied so as to compressively deform the first powder-compacted ring 208 such that the cross-sectional area of the element-insertion through-hole 115 is reduced, thereby unitarily attaching the first powder-compacted ring 208 and the protection cover 125 to the detection element 4. The thus-assembled first powder-compacted ring 208 and protection cover 125 can be used as an engagement section that projects laterally from the side surface of the detection element 4.

When the detection element 4 as a portion of the element unit 7 is to be disposed in the through-hole 109 of the metallic shell 102, engagement of the first powder-compacted ring 208, the ceramic holder 106, and the protection cover 125 with the stepped portion 107 axially positions the detection element 4 in the metallic shell 102. Such positioning of the detection element 4 in the metallic shell 102 eliminates the need to use a glass seal material, thereby preventing lowered sensor manufacturing efficiency, which could otherwise result from employing high-temperature thermal processing.

In the manufacturing method of the present embodiment, when the detection element 4 to which the first powder-compacted ring 208 and the like are integrally assembled is to be positioned in the through-hole 109 of the metallic shell 102, the detection element 4 can be disposed in the through-hole 109 of the metallic shell 102 irrespective of its angular orientation (an angular position around its axis). Therefore, there is no need to set the detection element 4 to a predetermined angular orientation, thereby facilitating the work of attaching the detection element 4 to the metallic shell 102.

Dimensions of the element unit fabrication jig 150 are determined such that the relative position between the detection element 4 and the first powder-compacted ring 208 (or the protection cover 125) as established at the time of assembly on the pedestal 151 becomes substantially equal to the relative position between the detection element 4 and the first powder-compacted ring 208 (or the protection cover 125) as established at the time of completing the air-fuel ratio sensor 2.

Thus, when the detection element 4 to which the first powder-compacted ring 208 and the protection cover 125 are integrally assembled is to be attached to the metallic shell 102, engaging the protection cover 125 with the stepped portion 107 can establish an appropriate, axial relative position between the detection element 4 and the metallic shell 102. This practice facilitates positioning (axial positioning) of the detection element 4 relative to the metallic shell 102, thereby rendering work less complicated.

In the present embodiment, in addition to the first powder-compacted ring 208, the protection cover 125 is integrally assembled to the detection element 4, so that the first powder-compacted ring 208 and the protection cover 125 can be used as an engagement section of the detection element 4. As compared with an engagement section implemented only by the first powder-compacted ring 208, the engagement section composed of the first powder-compacted ring 208 and the protection cover 125 exhibits higher strength, thereby preventing the occurrence of fracture, such as cracking or chipping, in the process of manufacturing a sensor.

Furthermore, in the manufacturing method of the present embodiment, the protection cover 125 is disposed so as to cover (surround) the side surface of the first powder-compacted ring 208. Thus, when the first powder-compacted ring 208 is to be compressively deformed by use of the element unit fabrication jig 150, use of a member for surrounding the side surface of the first powder-compacted ring 208 becomes unnecessary. Thus, the structure of the element unit fabrication jig 150 can be simplified, thereby reducing the cost of manufacturing a sensor.

In the air-fuel ratio sensor 2, the bottom portion 126 of the protection cover 125 formed of a metallic material is disposed between the ceramic holder 106 and the metallic shell 102 (specifically, the stepped portion 107). The thus-disposed bottom portion 126 of the protection cover 125 functions as a packing that prevents formation of a clearance between the ceramic holder 106 and the metallic shell 102 (specifically, the stepped portion 107), thereby enhancing gastightness of a sensor.

Furthermore, according to the method of manufacturing a sensor of the present embodiment, after the first powder-compacted ring 208 is integrally assembled to the detection element 4, the annular second powder-compacted ring 210 is fitted to the detection element 4, so that the second powder-compacted ring 210 can be supported by the first powder-compacted ring 208. In other words, when the second powder-compacted ring 210 is fitted to a rear end portion of the detection element 4 while the front end of the detection element 4 faces downward, the second powder-compacted ring 210 is disposed around the detection element 4 while resting on the first powder-compacted ring 208.

In the case where, at a stage before disposing the detection element 4 in the through-hole 109 of the metallic shell 102, the second powder layer 110 can be disposed around the detection element 4 as described above, the disposed condition of the second powder-compacted ring 210 in relation to the detection member 4 can be readily checked, so that the second powder-compacted ring 210 can be disposed in an appropriate condition.

Furthermore, employment of the second powder layer 110 (second powder-compacted ring 210) yields the following effect. In addition to the bottom portion 126 of the protection cover 125, the second powder layer 110 is caused to fill under pressure the space between the detection element 4 and the metallic shell 102, thereby effectively enhancing gastightness between the detection element 4 and the metallic shell 102.

While the present invention has been described with reference to the above embodiment, the present invention is not limited thereto. The present invention may be embodied in various other forms.

Figure 8:
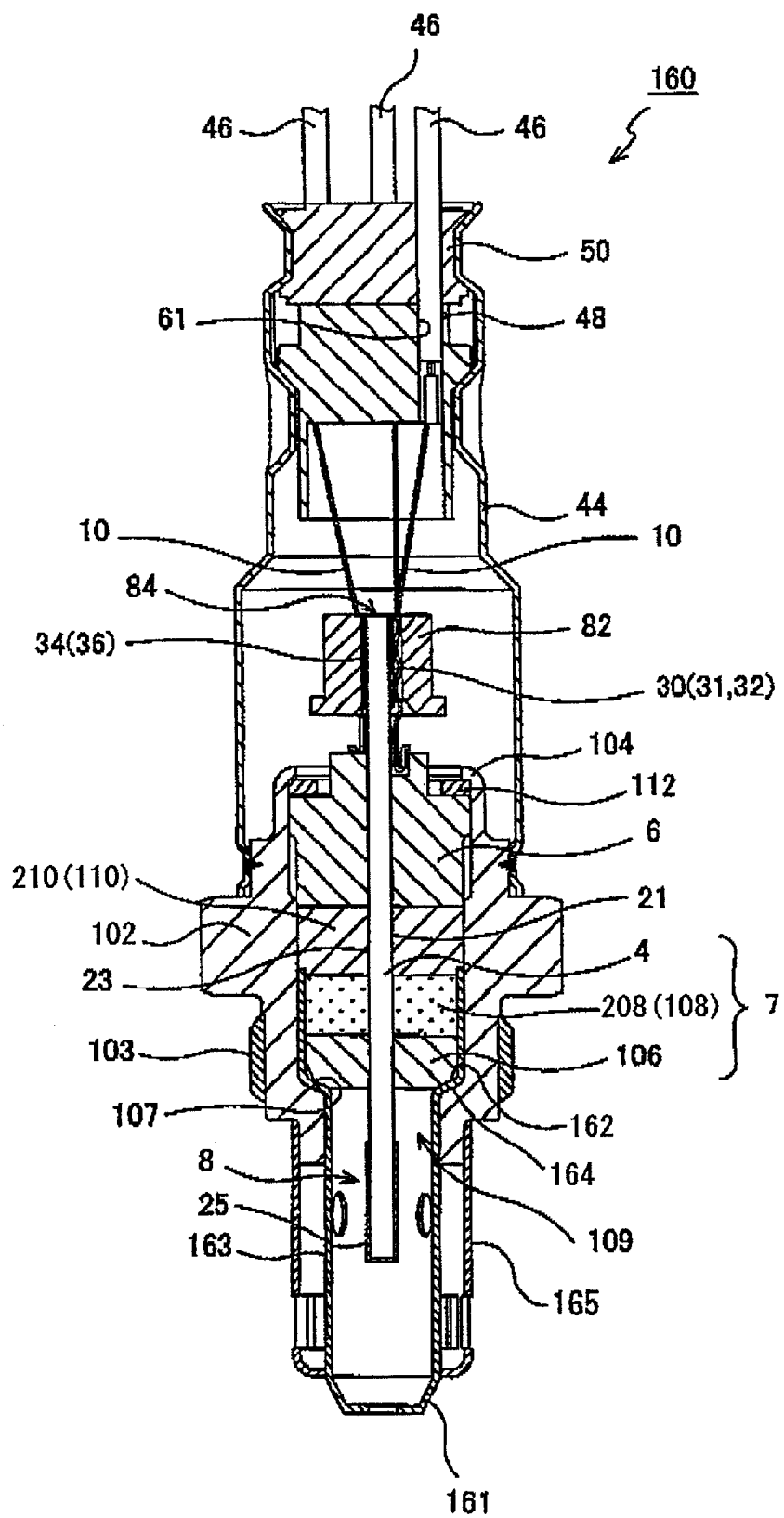
FIG. 8 is a sectional view showing the overall configuration of a second full-range air-fuel ratio sensor of the invention.

For example, the protector section that covers the detection portion of the detection element may be formed integrally with the protection cover. FIG. 8 is a sectional view showing the overall configuration of a second full-range air-fuel ratio sensor 160 including a second protection cover 161, which is configured such that the protection cover and the protector section are formed integrally with each other.

The second full-range air-fuel ratio sensor 160 is configured similarly to the full-range air-fuel ratio sensor 2 in the above-described embodiment (hereinafter also referred to as the first embodiment) except that the protection cover 125 and the inner protector 43 are replaced with the second protection cover 161, and the outer protector 42 is replaced with a second outer protector 165. In FIG. 8, members that are used in common with the first embodiment are denoted by common reference numerals.

The second protection cover 161 includes a cover portion 162, which assumes a shape similar to that of the above-mentioned protection cover 125, and a protector portion 163, which extends frontward from the cover portion 162. The cover portion 162 includes a cover-side engagement portion 164, which corresponds to the bottom portion 126 of the protection cover 125 in the first embodiment.

The protector portion 163 extends frontward from an opening portion of the cover-side engagement portion 164 and assumes a tubular shape whose front end is closed. The protector portion 163 has a plurality of hole portions formed at a side wall portion in order to allow passage of gas to be measured therethrough. The outside diameter of the protector portion 163 is substantially equal to the inside diameter of a front-end opening portion of the through-hole 109 of the metallic shell 102 and is smaller than that of the inner protector 43 in the first embodiment.

Next, the second outer protector 165 assumes a shape substantially similar to that of the outer protector 42 in the first embodiment and is smaller in outside diameter than the outer protector 42.

In the process of manufacturing the second full-range air-fuel ratio sensor 160, in a step that corresponds to the second step in fabrication of the element unit in the first embodiment, the second protection cover 161 is disposed such that the cover portion 162 covers the side surface of the first powder-compacted ring 208 and the side surface of the ceramic holder 106 and such that the protector portion 163 covers the detection portion 8 of the detection element 4.

According to the method of manufacturing a sensor in which the second protection cover 161 configured such that the cover portion 162 and the protector portion 163 are formed integrally with each other is used, the work of disposing the cover portion 162 at a position covering the side surface of the first powder-compacted ring 208 and the work of disposing the protector portion 163 at a position covering the detection portion 8 of the detection element 4 can be performed simultaneously by a single operation. As compared with the case where the protection cover and the protector section are individually provided, use of the second protection cover 161, which is configured such that the protector portion and the cover portion are formed integrally with each other, can reduce the number of working steps in the process of manufacturing a sensor.

Since, at an intermediate stage of manufacture of a sensor, the detection element 4 is covered and protected with the protector portion 163, fracture of the detection element 4 can be prevented in the subsequent course of manufacture. Particularly, when the detection element 4 is to be disposed in the through-hole 109 of the metallic shell 102, accidental contact between the detection element 4 and the metallic shell 102 can be prevented. Therefore, the work of attaching the detection element 4 to the metallic shell 102 does not require special attention to avoid contact between the detection element 4 and the metallic shell 102, thereby rendering the attachment work less complicated.

Furthermore, as compared with the case where the protection cover and the protector section are individually provided, use of the second protection cover 161, which is configured such that the cover portion 162 and the protector portion 163 are formed integrally with each other, can reduce the number of component members of a sensor, thereby curtailing the cost of manufacturing components and thus reducing the cost of manufacturing the sensor.

In the second full-range air-fuel ratio sensor 160, the second protection cover 161 includes the cover-side engagement portion 164 to be engaged with the stepped portion 107 of the metallic shell 102, thereby preventing the cover portion 162 from dropping out frontward from the metallic shell 102. The protector portion 163, which is formed integrally with the cover portion 162, does not drop off from the metallic shell 102 unless it is cut apart from the cover portion 162.

Thus, as compared with the full-range air-fuel ratio sensor 2, in which the inner protector 43 is joined to the metallic shell 102 by means of welding or the like, the second full-range air-fuel ratio sensor 160 has a structure such that the protector portion 163 hardly drops off, thereby preventing dropping-off of the protector section 163, which could otherwise result from influence of an external force. Therefore, the detection element 4 can be reliably protected by means of the protector portion 163.

Even when the second full-range air-fuel ratio sensor 160 is used in an environment in which an external force tends to be imposed on the detection element 4, the protector portion can protect the detection element 4 from the influence of an external force, so that the second full-range air-fuel ratio sensor 160 is suited for applications that require high gastightness.

A sensor of another embodiment uses a protection cover whose bottom portion assumes the form of a plane perpendicular to the axial direction at a stage before the talc ring is compressed to thereby be integrally assembled to the detection element. In other words, referring to FIG. 5, at a stage before the fourth step in fabricating the element unit, the shape of the bottom portion of the protection cover is not limited to a taper shape, but may assume any shape so long as, when the element unit is completed, the shape of the bottom portion is suited for engaging the stepped portion of the metallic shell.

Preferably, a metallic material used to form the protection cover is elastically deformable and can endure use in a high-temperature environment.

In the above-described embodiments, the material used to form the first powder layer 108, which corresponds to the first powder-compacted ring 208, and the second powder layer 110, which corresponds to the second powder-compacted ring 210, is not limited to talc powder. For example, a hexagonal-system boron nitride powder may be used.

Figure 9:
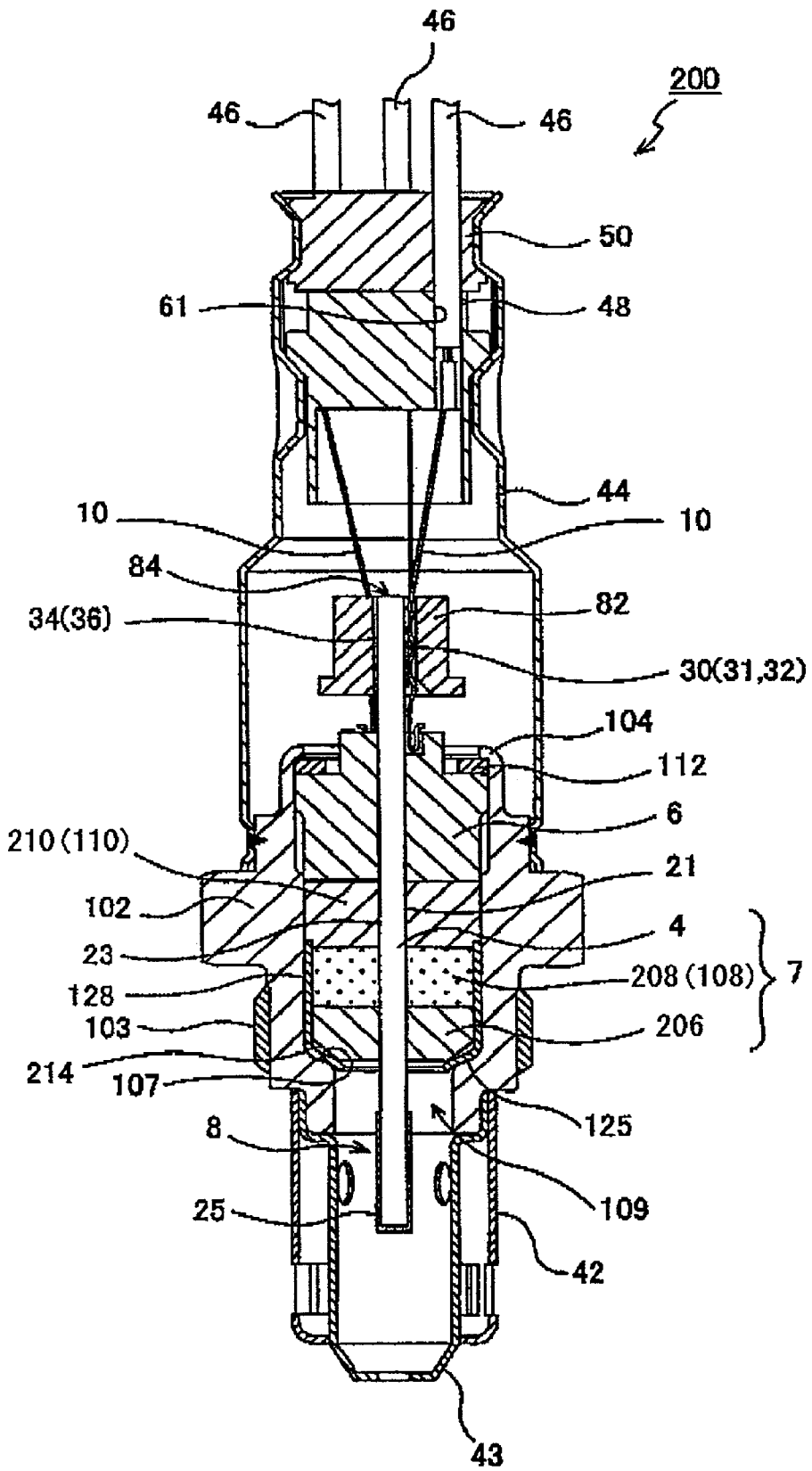
FIG. 9 is a sectional view showing the overall configuration of a third full-range air-fuel ratio sensor of the invention including a second ceramic holder.
Figure 10:
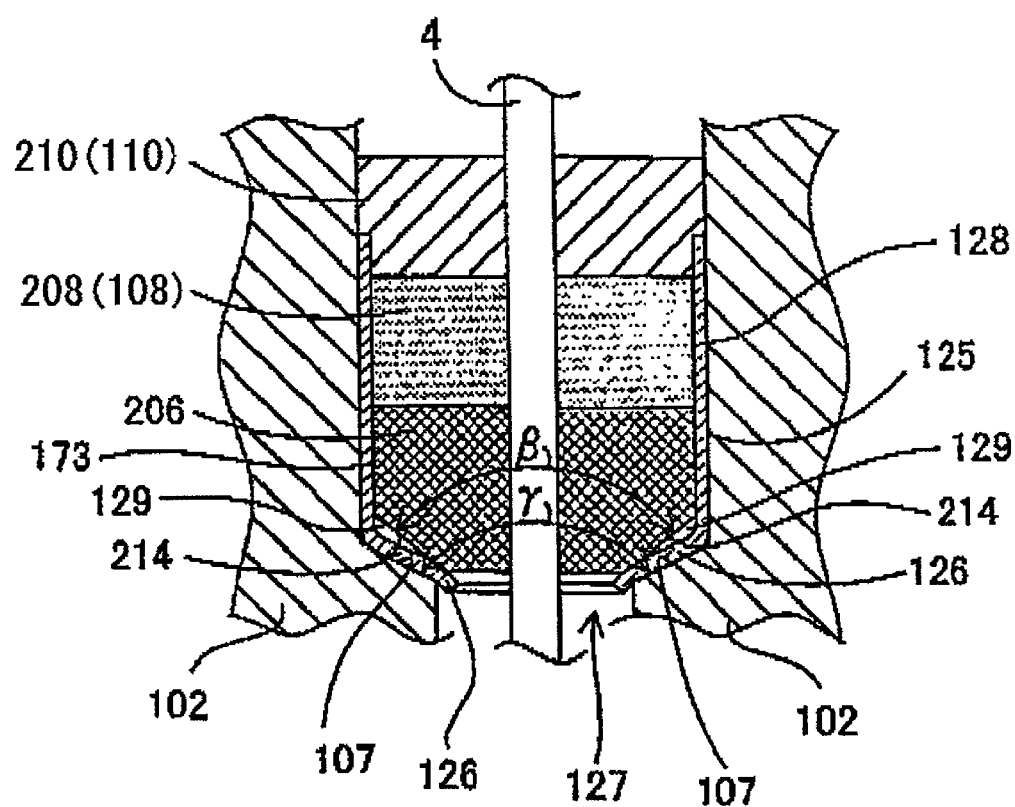
FIG. 10 is an enlarged sectional view of a portion of the third full-range air-fuel ratio sensor in which the second ceramic holder is disposed.

The ceramic holder disposed so as to surround the detection element from all radial directions is not limited to those having a plurality of taper surfaces (the front-end taper surface 114, the second taper surface 171) on the front end face, as the ceramic holder 106 of the first embodiment. FIG. 9 is a sectional view showing the overall configuration of a third full-range air-fuel ratio sensor 200 including a second ceramic holder 206, which has a single taper surface formed on the front end face thereof. FIG. 10 is an enlarged sectional view of a portion of the third full-range air-fuel ratio sensor 200 in which the second ceramic holder 206 is disposed.

Notably, the third full-range air-fuel ratio sensor 200 can be configured by replacing the ceramic holder 106 of the full-range air-fuel ratio sensor 2 of the first embodiment with the second ceramic holder 206. In FIGS. 9 and 10, those members identical with those of the first embodiment are denoted by the same reference numerals.

The second ceramic holder 206 is formed into an annular shape having an axially extending insertion through-hole portion. A single taper surface 214 is formed on the front end face of the second ceramic holder 206. The taper surface 214 faces frontward, and its diameter decreases frontward. Notably, the second ceramic holder 206 is configured in the same manner as the ceramic holder 106, except for the front end face.

The stepped portion 107 of the metallic shell 102 of the third full-range air-fuel ratio sensor 200 has a taper surface that is inclined relative to a plane perpendicular to the axial direction. The taper surface faces rearward, and its diameter increases rearward. The open angle γ of the taper surface of the stepped portion 107 is set to 120 [degree]. The open angle β of the single taper surface 214 of the second ceramic holder 206 is set to 90 [degree]. That is, the open angle β of the single taper surface 214 of the second ceramic holder 206 is set to an angle smaller than the open angle γ of the stepped portion 107 of the metallic shell 102.

Therefore, when the flange section (the powder-compacted filler layer 108, the second ceramic holder 206, and the protection cover 125) is assembled to the detection element 4, an annular clearance 129 extending along the inner circumferential surface of the protection cover 125 is formed between the single taper surface 214 of the second ceramic holder 206 and the inner circumferential surface of a connection portion between the bottom portion 126 and the side portion 128 of the protection cover 125.

As described above, by virtue of use of the second ceramic holder 206, which forms the clearance 129 between the taper surface 214 of the second ceramic holder 206 and the inner circumferential surface of the protection cover 125, even when the protection cover 125 partially swells and deforms inward in the vicinity of the connection portion between the bottom portion 126 and the side portion 128 of the protection cover 125, the above construction prevents the swollen and deformed portion from coming into contact with the second ceramic holder 206.

Accordingly, by virtue of the method of manufacturing the third full-range air-fuel ratio sensor 200 including the second ceramic holder 206, even when the protection cover 125 is deformed in the course of a manufacturing process, the second ceramic holder 206 does not break due to the deformation, whereby the incident rate of defective products can be lowered, and thus, the production efficiency of sensors can be improved.

This application is based on Japanese Patent Application No. 2003-185724 filed Jun. 27, 2003, incorporated herein by reference in its entirety.

What is claimed is:

1. A sensor comprising:
   a detection element having a detection portion formed at a front end portion directed to an object to be measured, and an electrode terminal portion formed at a rear end portion thereof;
   a first powder layer and a second powder layer circumferentially covering a portion of the detection element located between the detection portion and the electrode terminal portion;
   a protection cover circumferentially covering the first powder layer; and
   a metallic shell having a through-hole for accommodating the first powder layer, the second powder layer and the protection cover, wherein
   the first powder layer fills a space between the protection cover and the detection element; and
   the second powder layer is larger in diameter than the first powder layer, and fills a space so as to contact both an inner surface of the metallic shell and an outer surface of the detection element.

* * * * *